(12) United States Patent
McGregor et al.

(10) Patent No.: US 11,135,003 B2
(45) Date of Patent: Oct. 5, 2021

(54) SYSTEM AND METHOD FOR INDEPENDENT OR SIMULTANEOUS CONTROL OF MULTIPLE RADIOFREQUENCY PROBES DURING AN ABLATION PROCEDURE

(71) Applicant: Avent, Inc., Alpharetta, GA (US)

(72) Inventors: Lisa M. McGregor, Chamblee, GA (US); Lee Rhein, Hollywood, FL (US); Tyler W. Crone, Atlanta, GA (US); Joseph A. Cesa, Franklin, MA (US); Christopher W. Thurrott, Townsend, MA (US); Morgan Rudolph, Nashua, NH (US); Scott Woodruff, Chicago, IL (US)

(73) Assignee: AVENT, INC., Alpharetta, GA (US)

( * ) Notice: Subject to any disclaimer, the term of this patent is extended or adjusted under 35 U.S.C. 154(b) by 377 days.

(21) Appl. No.: 16/034,914

(22) Filed: Jul. 13, 2018

(65) Prior Publication Data

US 2020/0015879 A1    Jan. 16, 2020

(51) Int. Cl.
*A61B 18/14* (2006.01)
*A61B 34/00* (2016.01)
(Continued)

(52) U.S. Cl.
CPC .............. *A61B 18/14* (2013.01); *A61B 34/25* (2016.02); *A61B 90/06* (2016.02); *A61B 90/39* (2016.02);
(Continued)

(58) Field of Classification Search
CPC ......... A61B 18/14; A61B 34/25; A61B 90/06; A61B 90/39; A61B 2090/062;
(Continued)

(56) References Cited

U.S. PATENT DOCUMENTS 5,334,181 A    8/1994   Rubinsky et al.
5,819,741 A    10/1998  Karlsson et al.
(Continued)

FOREIGN PATENT DOCUMENTS

EP    1 749 492 A1    2/2007
EP    2 942 023 A2    11/2015
(Continued)

OTHER PUBLICATIONS

International Search Report and Written Opinion for PCT/US2019/040236, dated Oct. 14, 2019, 17 pages.

*Primary Examiner* — Linda C Dvorak
*Assistant Examiner* — Nils A Potter
(74) *Attorney, Agent, or Firm* — Meunier Carlin & Curfman LLC

(57) ABSTRACT

A system and method for delivering energy to a patient's body includes a plurality of probes each having an elongate member with a distal region having an electrically non-conductive outer circumferential portion and a proximal region. Each of the plurality of probes further includes an electrically conductive energy delivery device extending distally from the electrically non-conductive outer circumferential portion for delivering one of electrical and radiofrequency energy to the patient's body. The energy delivery devices further include an electrically conductive outer circumferential surface. The system also includes at least one controller communicatively coupled to each of the plurality of probes. The controller includes a user interface having a control screen. The control screen includes an independent control module and a simultaneous control module that allows a user to select between independent control or simultaneous control of the plurality of probes.

20 Claims, 9 Drawing Sheets

(51) Int. Cl.
*A61B 90/00* (2016.01)
*A61B 18/00* (2006.01)

(52) U.S. Cl.
CPC ............ *A61B 2018/00023* (2013.01); *A61B 2018/0044* (2013.01); *A61B 2018/00077* (2013.01); *A61B 2018/00083* (2013.01); *A61B 2018/00577* (2013.01); *A61B 2018/00642* (2013.01); *A61B 2018/00702* (2013.01); *A61B 2018/00714* (2013.01); *A61B 2018/00755* (2013.01); *A61B 2018/00791* (2013.01); *A61B 2018/00875* (2013.01); *A61B 2090/062* (2016.02); *A61B 2090/3966* (2016.02)

(58) Field of Classification Search
CPC .. A61B 2090/3966; A61B 2018/00023; A61B 2018/00077; A61B 2018/00083; A61B 2018/0044; A61B 2018/00577; A61B 2018/00642; A61B 2018/00702; A61B 2018/00714; A61B 2018/00755; A61B 2018/00791; A61B 2018/00875; A61B 2017/00199; A61B 2017/00225; A61B 2018/1273; A61B 2018/124; A61B 18/148; A61B 18/1206; A61B 2018/00005; A61B 2018/00648; A61B 2018/00654; A61B 2018/00666; A61B 2018/00744; A61B 2018/00761; A61B 2018/00898; A61B 2018/00779; A61B 2018/00797; A61B 2018/00863; A61B 2018/00339; G16H 20/40; G16H 20/30; G16H 40/63
USPC .......................................................... 606/41
See application file for complete search history.

(56) References Cited

U.S. PATENT DOCUMENTS

| | | | |
|---|---|---|---|
| 5,871,481 A | 2/1999 | Kammemberg et al. | |
| 5,954,719 A | 9/1999 | Chen et al. | |
| 6,356,790 B1 | 3/2002 | Maguire et al. | |
| 6,625,482 B1 | 9/2003 | Panescu et al. | |
| 6,679,269 B2 | 1/2004 | Swanson | |
| 7,122,031 B2 | 10/2006 | Edwards et al. | |
| 8,603,087 B2 | 12/2013 | Rubinsky et al. | |
| 8,657,814 B2 | 2/2014 | Werneth et al. | |
| 8,845,630 B2 | 9/2014 | Mehta et al. | |
| 9,005,128 B2 | 4/2015 | Imamura et al. | |
| 9,008,793 B1 | 4/2015 | Cosman, Sr. et al. | |
| 9,308,372 B2 | 4/2016 | Sparks et al. | |
| 9,333,031 B2 | 5/2016 | Salahieh et al. | |
| 9,393,071 B1 | 7/2016 | Boveja et al. | |
| 9,427,284 B2 | 8/2016 | Moss et al. | |
| 9,495,059 B2 | 11/2016 | Shikhman et al. | |
| 9,510,887 B2 | 12/2016 | Burnett et al. | |
| 9,510,909 B2 | 12/2016 | Grant et al. | |
| 9,522,048 B1 | 12/2016 | Schmit et al. | |
| 9,532,831 B2 | 1/2017 | Reinders et al. | |
| 9,547,752 B2 | 1/2017 | Sandhu et al. | |
| 9,592,387 B2 | 3/2017 | Skelton et al. | |
| 9,597,145 B2 | 3/2017 | Nelson et al. | |
| 2003/0212390 A1 | 11/2003 | Chen et al. | |
| 2005/0177209 A1 | 8/2005 | Leung et al. | |
| 2007/0129633 A1 | 6/2007 | Lee et al. | |
| 2009/0138011 A1 | 5/2009 | Epstein | |
| 2010/0016926 A1 | 1/2010 | Rittman, III | |
| 2011/0172659 A1 | 7/2011 | Brannan | |
| 2012/0260293 A1* | 10/2012 | Young | H04N 5/4403 725/52 |
| 2013/0018368 A1 | 1/2013 | Chan et al. | |
| 2013/0030426 A1 | 1/2013 | Gallardo et al. | |
| 2013/0138097 A1 | 5/2013 | Mathur et al. | |
| 2013/0165919 A1 | 6/2013 | Epstein | |
| 2013/0335441 A1 | 12/2013 | Zalev et al. | |
| 2014/0330266 A1 | 11/2014 | Thompson et al. | |
| 2015/0057945 A1* | 2/2015 | White | G06K 9/00348 702/19 |
| 2015/0182740 A1 | 7/2015 | Mickelsen | |
| 2015/0297282 A1 | 10/2015 | Cadouri | |
| 2015/0320481 A1 | 11/2015 | Cosman, Jr. et al. | |
| 2016/0048635 A1 | 2/2016 | Warner et al. | |
| 2016/0354142 A1 | 12/2016 | Pearson et al. | |
| 2017/0065352 A1 | 3/2017 | Razzaque et al. | |
| 2018/0085188 A1* | 3/2018 | Boutoussov | A61C 1/0015 |
| 2018/0110554 A1* | 4/2018 | Zarins | A61B 18/1482 |

FOREIGN PATENT DOCUMENTS

| | | | | |
|---|---|---|---|---|
| WO | WO 2014/144359 A1 | 9/2014 | | |
| WO | WO 2016/090175 A1 | 6/2016 | | |
| WO | WO 2018/116273 A1 | 6/2018 | | |
| WO | WO-2018116273 A1 * | 6/2018 | | ......... A61B 18/1206 |

* cited by examiner

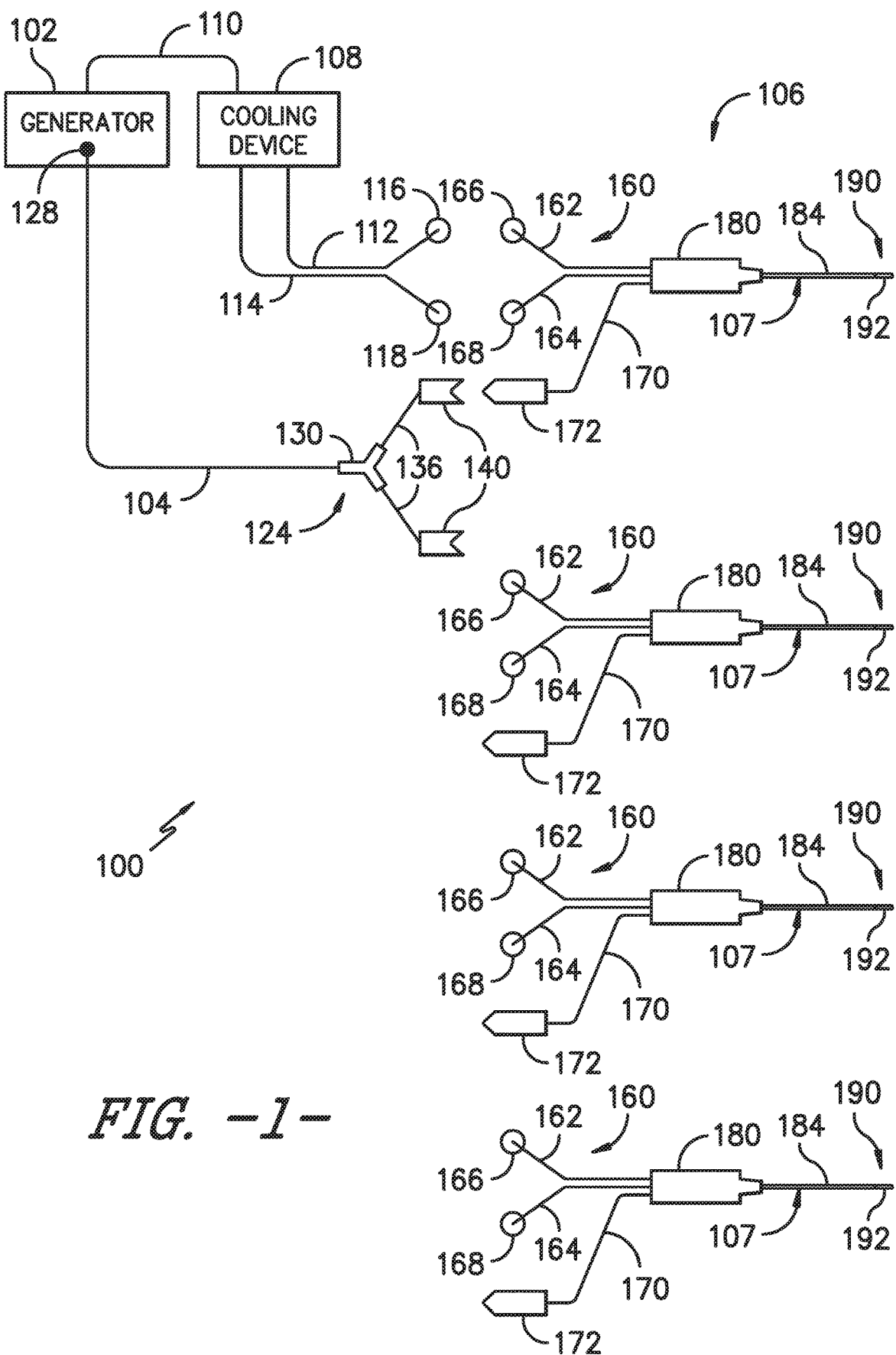
FIG. -1-

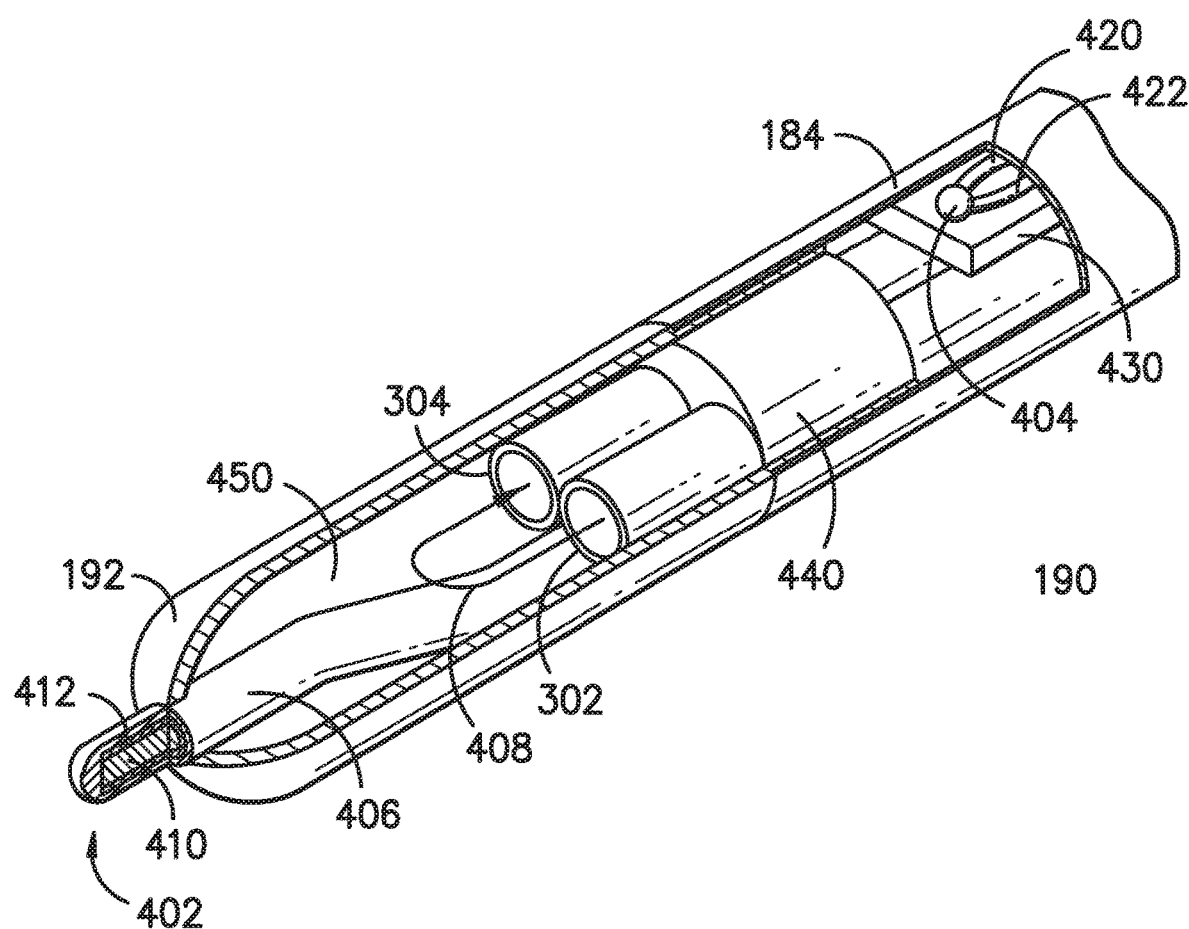
FIG. -2-

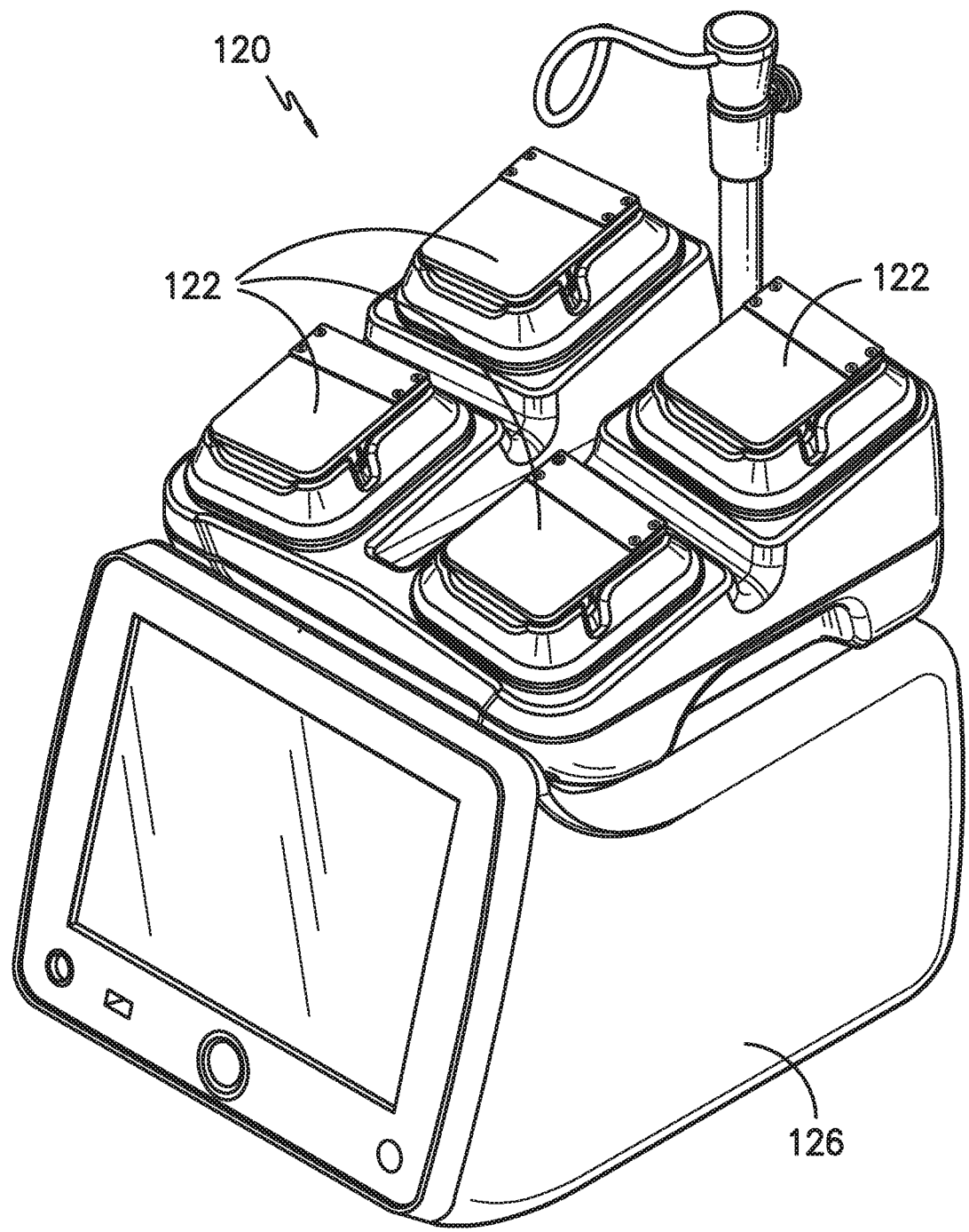
FIG. -3-

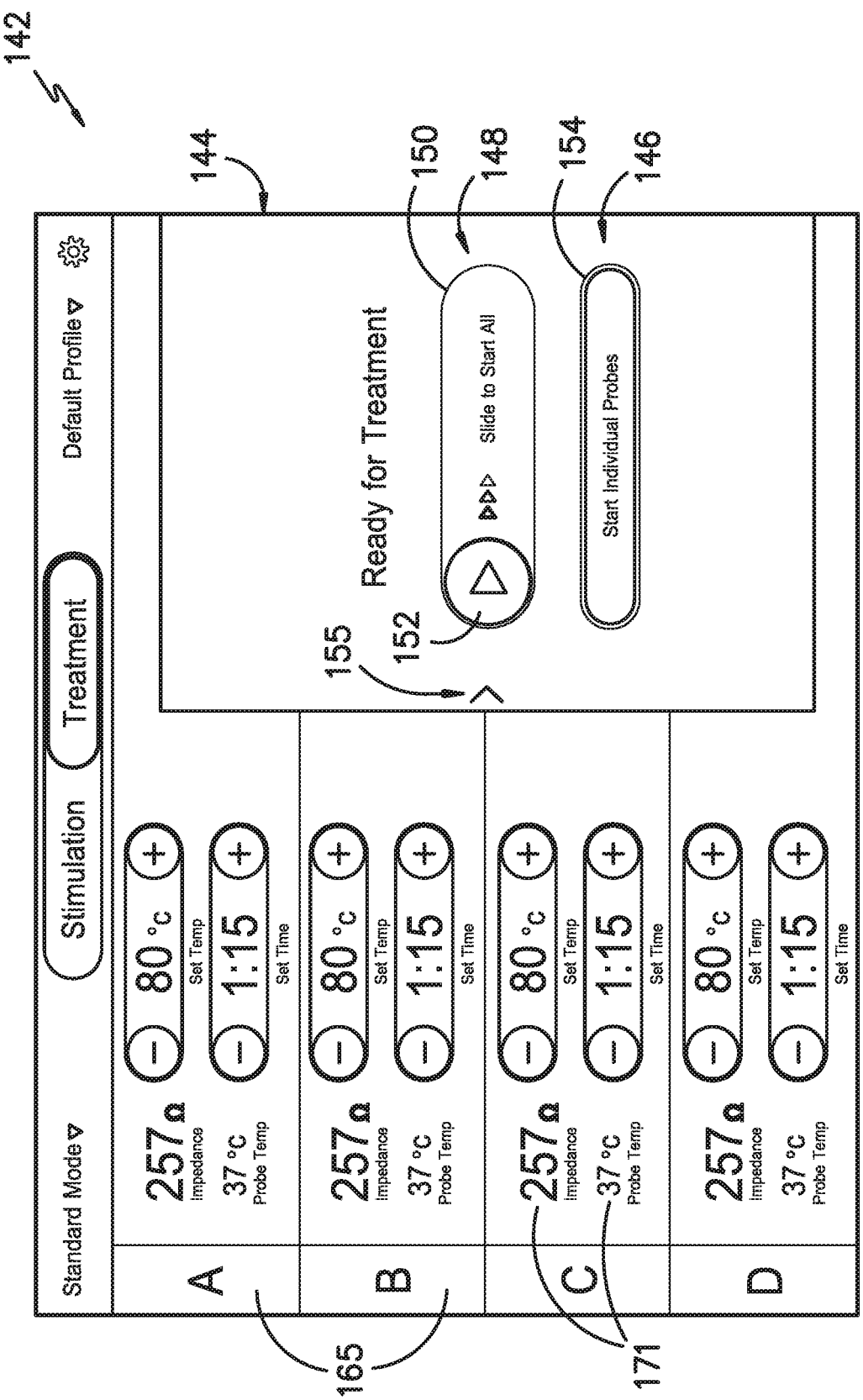
FIG. -4-

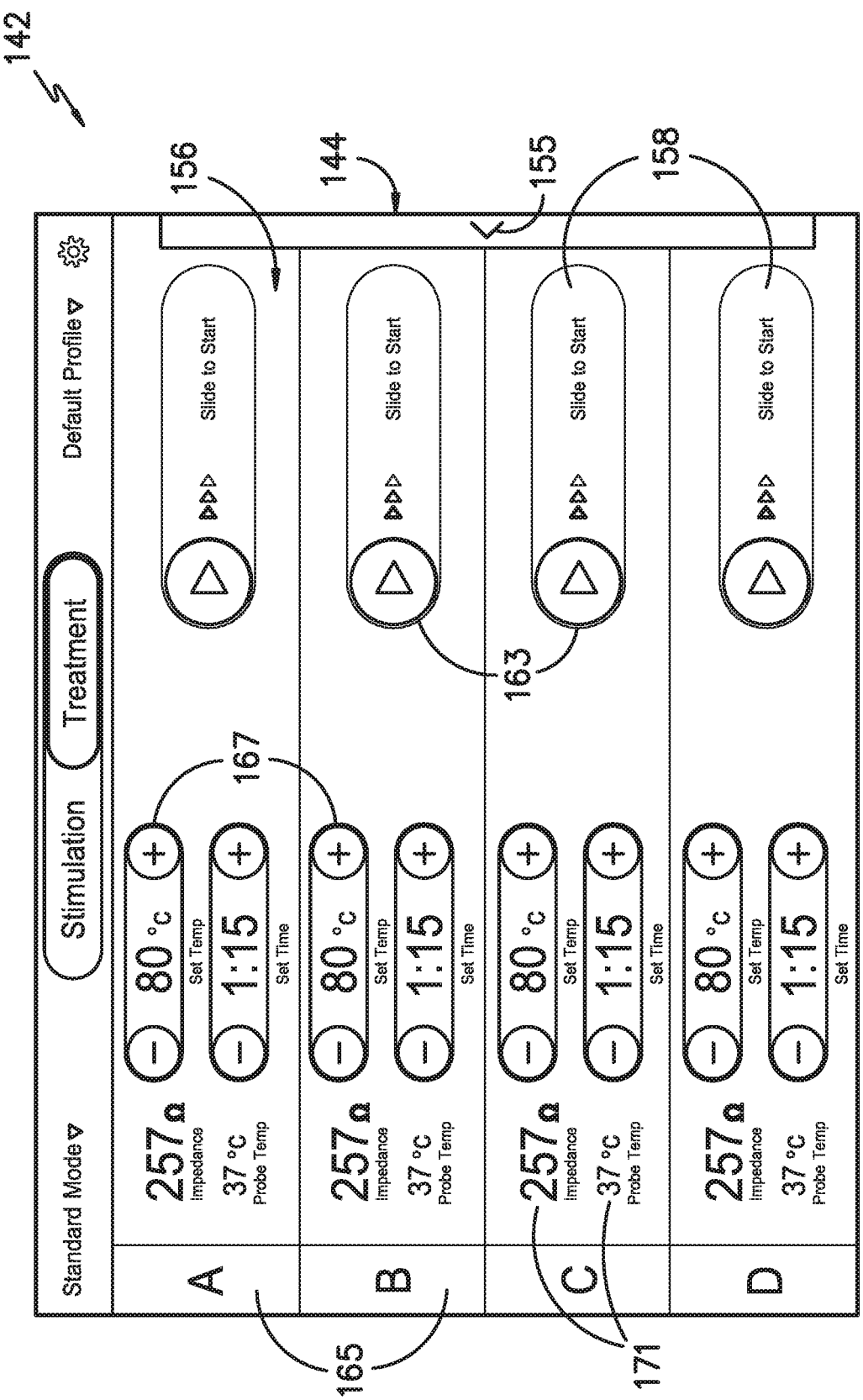
FIG. -5-

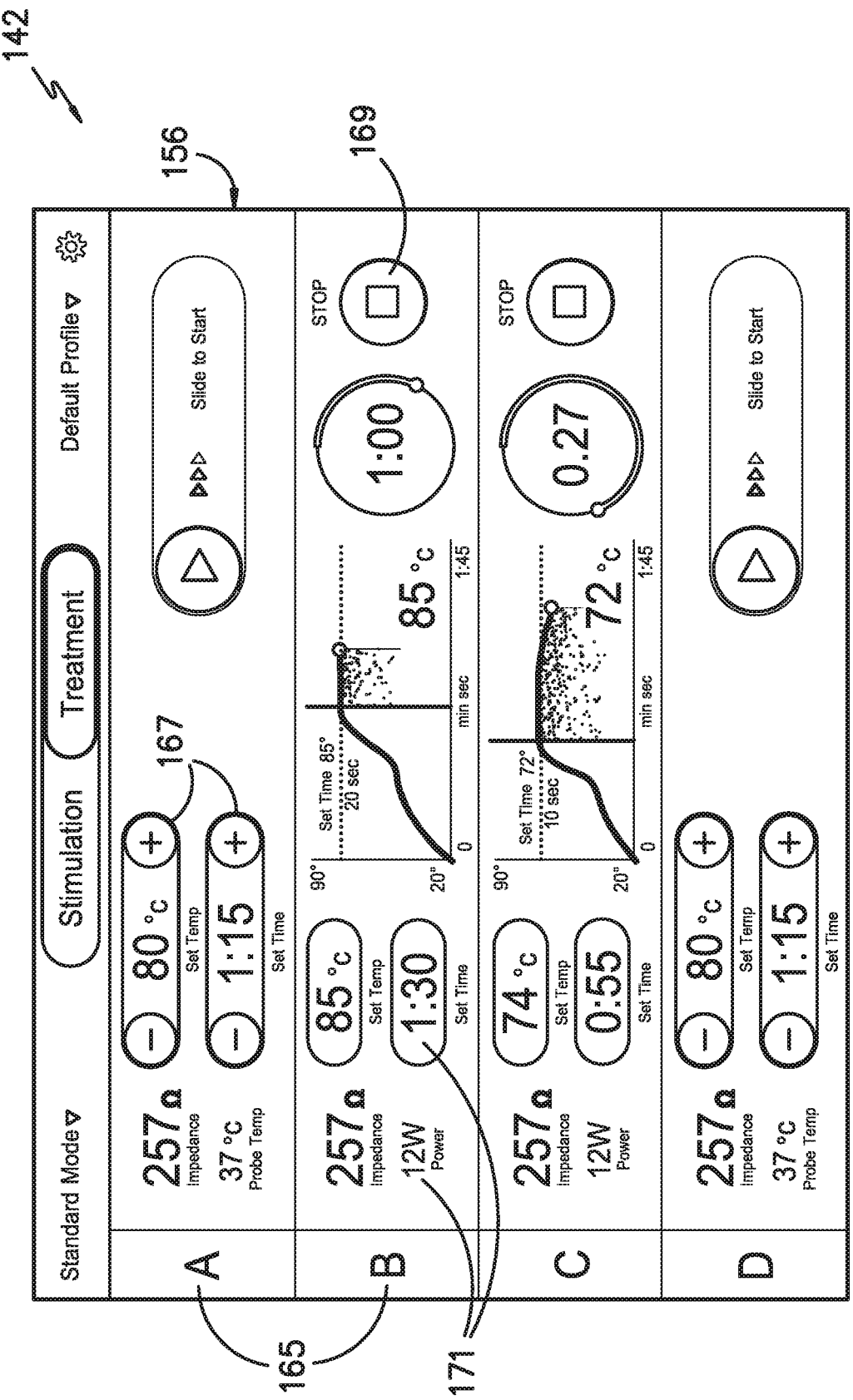
FIG. -6-

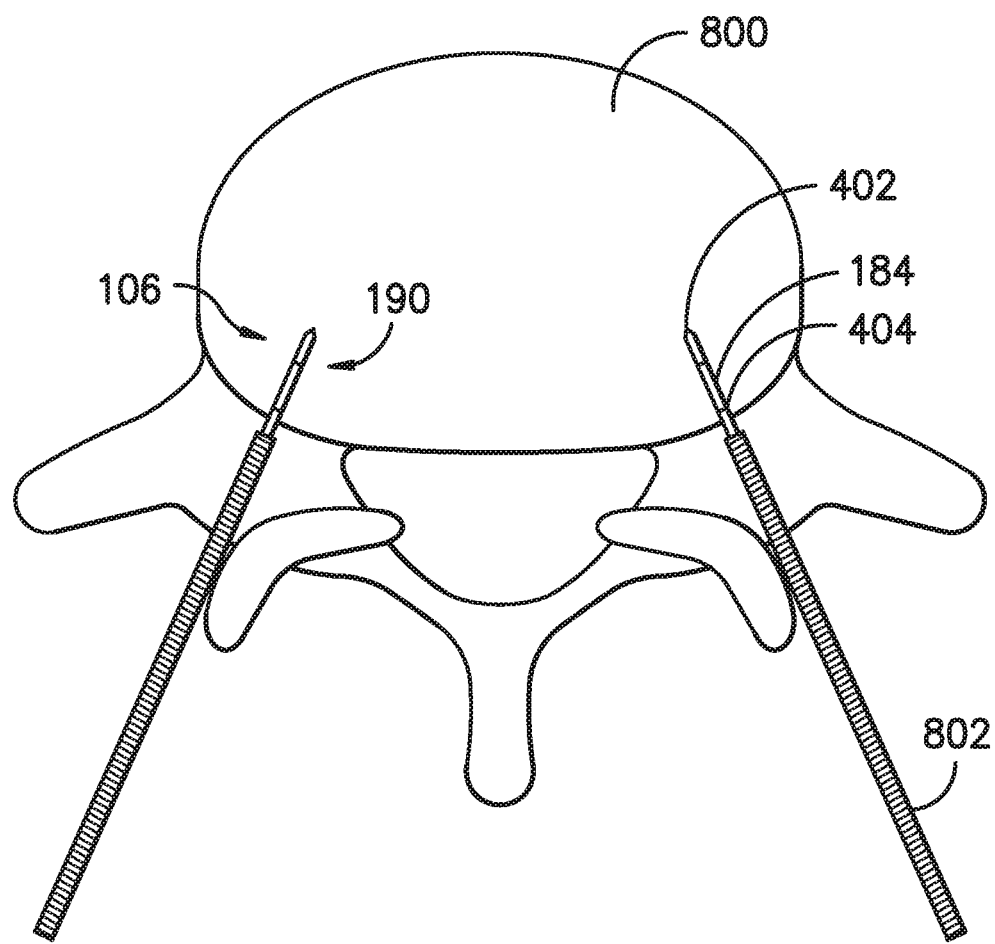
FIG. —7—

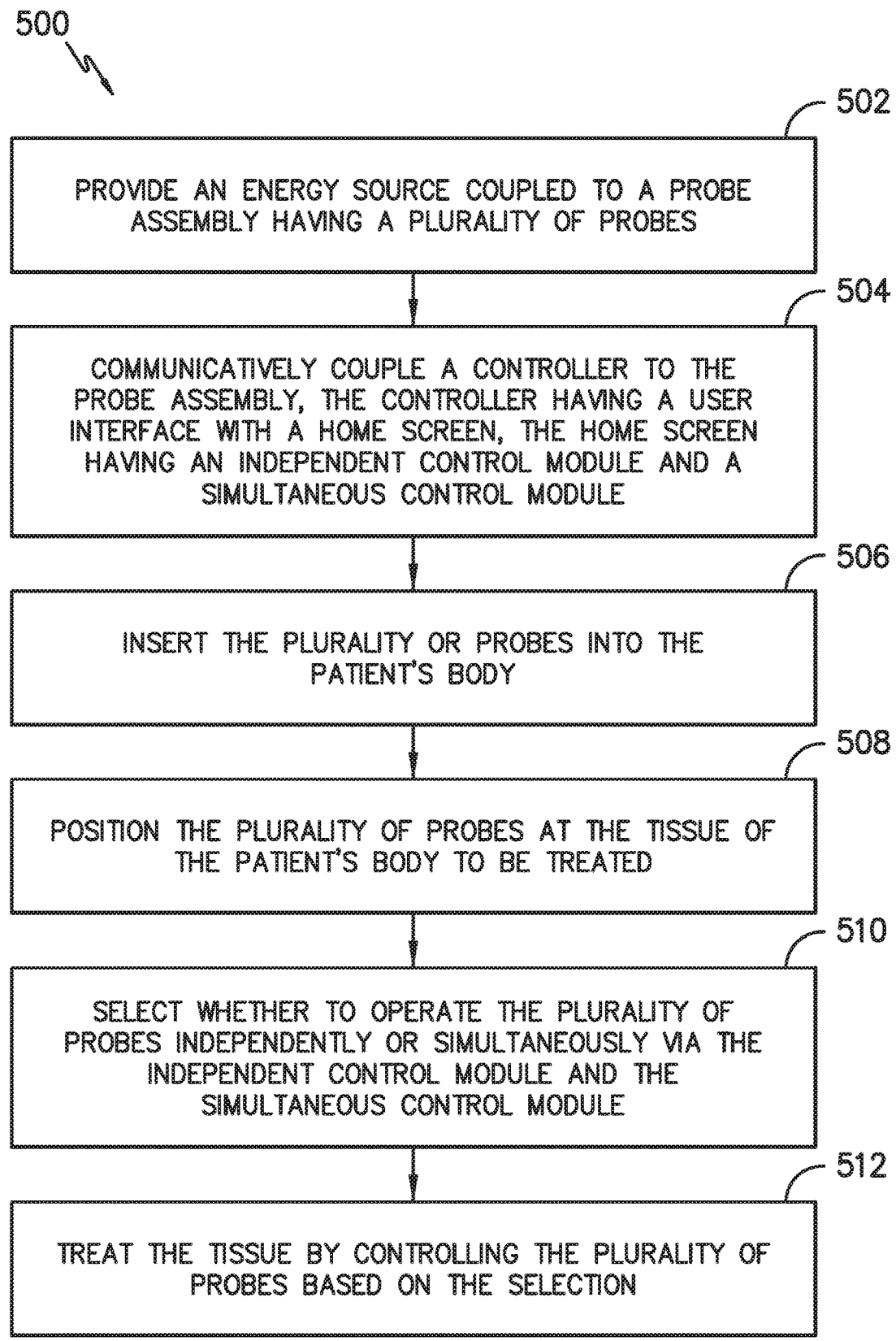
FIG. -8-

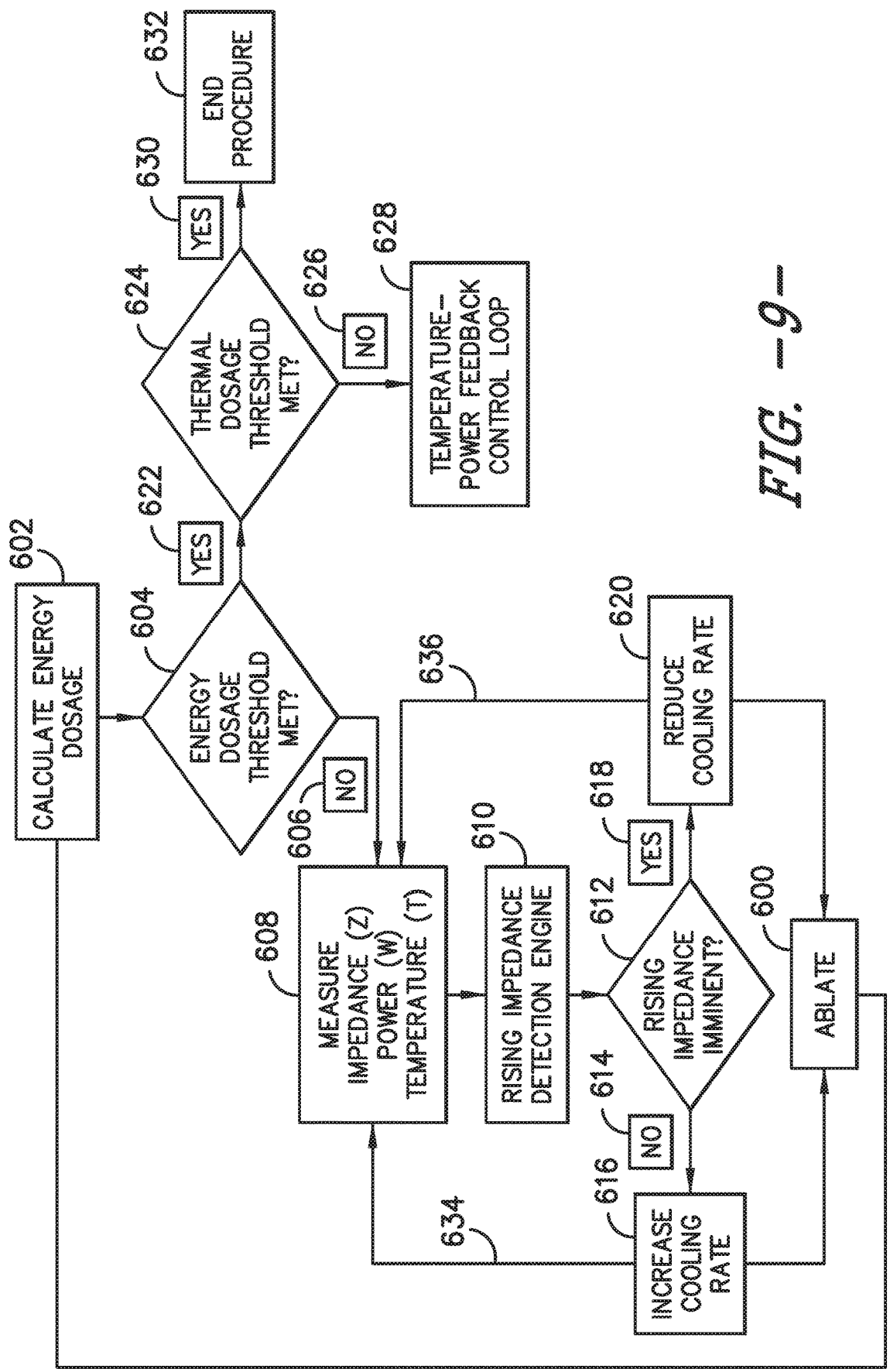
FIG. -9-

SYSTEM AND METHOD FOR INDEPENDENT OR SIMULTANEOUS CONTROL OF MULTIPLE RADIOFREQUENCY PROBES DURING AN ABLATION PROCEDURE

FIELD OF THE INVENTION

The present invention relates generally to a system and method for applying energy for the treatment of tissue, and more particularly to a system and method for independent or simultaneous control of multiple radiofrequency probes during an ablation procedure.

BACKGROUND

Lower back injuries and chronic back pain are a major health problem resulting not only in a debilitating condition for the patient, but also in the consumption of a large proportion of funds allocated for health care, social assistance and disability programs. Disc abnormalities and pain may result from trauma, repetitive use in the workplace, metabolic disorders, inherited proclivity or aging. The existence of adjacent nerve structures and innervation of the disc are very important issues in respect to patient treatment for back pain.

A minimally invasive technique of delivering high-frequency electrical current has been shown to relieve localized pain in many patients. Generally, the high-frequency current used for such procedures is in the radio frequency (RF) range, i.e. between 100 kHz and 1 GHz and more specifically between 300-600 kHz. The RF electrical current is typically delivered from a generator via a plurality of connected electrodes that are placed in a patient's body, in a region of tissue that contains a neural structure suspected of transmitting pain signals to the brain. The electrodes generally include an insulated shaft with an exposed conductive tip to deliver the radio frequency electrical current. Tissue resistance to the current causes heating of tissue adjacent resulting in the coagulation of cells (at a temperature of approximately 45° C. for small unmyelinated nerve structures) and the formation of a lesion that effectively denervates the neural structure in question. Denervation refers to a procedure whereby the ability of a neural structure to transmit signals is affected in some way and usually results in the complete inability of a neural structure to transmit signals, thus removing the pain sensations.

To extend the size of a lesion, radiofrequency treatment may be applied in conjunction with a cooling mechanism, whereby a cooling means is used to reduce the temperature of the tissue near an energy delivery device, allowing a higher voltage to be applied without causing an unwanted increase in local tissue temperature. The application of a higher voltage allows regions of tissue further away from the energy delivery device to reach a temperature at which a lesion can form, thus increasing the size/volume of the lesion.

Such procedures can be done using any suitable number of probes, e.g. from one probe up to four probes at a time. If one of the probes encounters a condition that causes the probe to stop during its procedure, however, the probe remains inactive until all remaining probes have completed their procedures. Once the other probes have completed their procedures, a user can troubleshoot the problem probe and restart the problem probe's procedure. Unfortunately, such workflow requires the user to waste valuable time waiting for procedures to finish, adding probe procedure times together, which extends the overall time that the patient must endure the treatment procedure.

Thus, the present disclosure is directed to systems and methods for independent or simultaneous control of multiple radiofrequency probes during an ablation procedure that addresses the aforementioned issues.

SUMMARY OF THE INVENTION

Objects and advantages of the invention will be set forth in part in the following description, or may be obvious from the description, or may be learned through practice of the invention.

In one aspect, the present invention is directed to a system for delivering energy to a patient's body. The system includes a plurality of probes each having an elongate member with a distal region having an electrically non-conductive outer circumferential portion and a proximal region. Each of the plurality of probes further includes an electrically conductive energy delivery device extending distally from the electrically non-conductive outer circumferential portion for delivering one of electrical and radiofrequency energy to the patient's body. The energy delivery devices further include an electrically conductive outer circumferential surface. The system also includes at least one controller communicatively coupled to each of the plurality of probes. The controller includes a user interface having a collapsible control screen. The collapsible control screen includes an independent control module and a simultaneous control module that allows a user to select between independent control or simultaneous control of the plurality of probes.

In one embodiment, the simultaneous control module may include a simultaneous control selection panel that, upon selection by the user, is configured to start a treatment procedure for each of the plurality of probes simultaneously. In another embodiment, the simultaneous control selection panel may include a simultaneous control sliding bar.

In further embodiments, the independent control module may include an independent control selection panel that, upon selection by the user, is configured to start individual control of the plurality of probes. In such embodiments, once the user selects the independent control selection panel, the control screen collapses by engaging the control arrow and the user interface switches to an independent control screen. In another embodiment, the independent control screen may include an independent control panel for each of the plurality of probes. In additional embodiments, the independent control panel for each of the plurality of probes may include an independent sliding bar that, upon selection by the user, is configured to start a treatment procedure for one of the probes from the plurality of probes.

In another embodiment, the control screen may also include a control arrow that, when swiped in a first direction by a user, collapses the control screen. As such, if the user wants to reopen the collapsed control screen, the user can simply swipe the control arrow in a second direction opposite the first direction and the control screen will reappear.

In further embodiments, the simultaneous control selection panel and/or each of the independent control panels may include a display for displaying one or more real-time operating parameters of the treatment procedure. For example, in such embodiments, the one or more real-time operating parameters may include an actual temperature, an impedance, an actual time, a run time, a power output of the energy delivery device, a threshold temperature, or combinations thereof.

In several embodiments, each of the independent control panels may include one or more buttons for allowing the user to modify one or more of the operating parameters. In such embodiments, one of the one or more buttons may include a stop button for stopping the treatment procedure.

In another aspect, the present disclosure is directed to a method of treating tissue of a patient's body. The method includes providing an energy source coupled to a probe assembly. The probe assembly includes a plurality of probes, with each probe having an elongate member with a distal region and a proximal region. The distal region has an electrically-conductive energy delivery device for delivering one of electrical and radiofrequency energy to the patient's body. The method further includes communicatively coupling a controller to the probe assembly. The controller has a user interface with a control screen. The control screen has an independent control module and a simultaneous control module. The method also includes inserting the plurality of probes into the patient's body and positioning the plurality of probes at the tissue of the patient's body to be treated. Further, the method includes selecting whether to operate the plurality of probes independently or simultaneously via the independent control module and the simultaneous control module. As such, the method includes treating the tissue by controlling the plurality of probes based on the selection. It should also be understood that the method may further include any of the additional steps and/or features as described herein.

In yet another aspect, the present disclosure is directed to a controller for controlling a plurality of radiofrequency probes during a treatment procedure. The controller includes a user interface having a control screen. The control screen includes an independent control module and a simultaneous control module that allows a user to select between independent control or simultaneous control of the plurality of probes. As such, the simultaneous control module includes a simultaneous control selection panel that, upon selection by the user, is configured to start a treatment procedure for each of the plurality of probes simultaneously. In addition, the independent control module includes an independent control selection panel that, upon selection by the user, is configured to start individual control of the plurality of probes such that the control screen collapses and the user interface switches to an independent control screen. It should also be understood that the controller may further include any of the additional features as described herein.

These and other features, aspects and advantages of the present invention will become better understood with reference to the following description and appended claims. The accompanying drawings, which are incorporated in and constitute a part of this specification, illustrate embodiments of the invention and, together with the description, explain the principles of the invention.

BRIEF DESCRIPTION OF THE DRAWINGS

A full and enabling disclosure of the present invention, including the best mode thereof, directed to one of ordinary skill in the art, is set forth in the specification, which refers to the appended figures, in which:

FIG. 1 illustrates a portion of one embodiment of a system for applying radio frequency electrical energy to a patient's body according to the present disclosure;

FIG. 2 illustrates a perspective cut-away view of one embodiment of a distal tip region of a probe assembly according to the present disclosure;

FIG. 3 illustrates a perspective view of one embodiment of a pump assembly according to the present disclosure;

FIG. 4 illustrates a representation of one embodiment of a user interface of a controller of the probe assembly according to the present disclosure, particularly illustrating the control screen of the user interface;

FIG. 5 illustrates a representation of one embodiment of a user interface of a controller of the probe assembly according to the present disclosure, particularly illustrating the independent control screen of the user interface;

FIG. 6 illustrates a representation of another embodiment of a user interface of a controller of the probe assembly according to the present disclosure, particularly illustrating the independent control screen of the user interface with certain treatment procedures of selective probes initiated;

FIG. 7 illustrates two probes placed within an intervertebral disc according to the present disclosure;

FIG. 8 illustrates a flow diagram of one embodiment of a method of treating tissue of a patient's body according to the present disclosure;

FIG. 9 illustrates a block diagram of one embodiment of a treatment procedure for actively controlling energy delivered to tissue in the patient's body by controlling an amount of energy delivered by the energy delivery devices and a flow rate of the pumps of the pump assembly according to the present disclosure.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this invention, a lesion refers to any effect achieved through the application of energy to a tissue in a patient's body, and the invention is not intended to be limited in this regard. Furthermore, for the purposes of this description, proximal generally indicates that portion of a device or system next to or nearer to a user (when the device is in use), while the term distal generally indicates a portion further away from the user (when the device is in use).

Referring now to the drawings, FIG. 1 illustrates a schematic diagram of one embodiment of a system 100 of the present invention. As shown, the system 100 includes a generator 102, a cable 104, at least one probe assembly 106 having a plurality of probes 107, one or more cooling devices 108, a pump cable 110, one or more proximal cooling supply tubes 112 and one or more proximal cooling return tubes 114. As shown in the illustrated embodiment, the generator 102 is a radio frequency (RF) generator, but may optionally be any energy source that may deliver other forms of energy, including but not limited to microwave energy, thermal energy, ultrasound and optical energy. In one embodiment, the generator 102 is operable to communicate with one more devices, for example with the probes 107 and the one or more cooling devices 108. Such communication may be unidirectional or bidirectional depending on the devices used and the procedure performed.

In addition, as shown, a distal region 124 of the cable 104 may include a splitter 130 that divides the cable 104 into two distal ends 136 such that the probes 107 can be connected thereto. A proximal end 128 of the cable 104 is connected to the generator 102. This connection can be permanent, whereby, for example, the proximal end 128 of the cable 104 is embedded within the generator 102, or temporary, whereby, for example, the proximal end 128 of cable 104 is connected to generator 102 via an electrical connector. The two distal ends 136 of the cable 104 terminate in connectors 140 operable to couple to the probes 107 and establish an electrical connection between the probes 107 and the generator 102. In alternate embodiments, the system 100 may include a separate cable for each probe assembly 106 being used to couple the probes 107 to the generator 102. Alternatively, the splitter 130 may include more than two distal ends. Such a connector is useful in embodiments having more than two devices connected to the generator 102, for example, if more than two probe assemblies are being used.

The cooling device(s) 108 may include any means of reducing a temperature of material located at and proximate to one or more of the probes 107. For example, as shown in FIG. 3, the cooling devices 108 may include a pump assembly 120 having one or more peristaltic pumps 122 operable to circulate a fluid from the cooling devices 108 through one or more proximal cooling supply tubes 112, the probes 107, one or more proximal cooling return tubes 114 and back to the one or more cooling devices 108. For example, as shown, the pump assembly 120 includes four peristaltic pumps 122 coupled to a power supply 126. In alternate embodiments, the pump assembly 120 may include only one peristaltic pump or greater than four pumps. The fluid may be water or any other suitable fluid.

Still referring to FIG. 1, the system 100 may include a controller for facilitating communication between the cooling devices 108 and the generator 102. In this way, feedback control is established between the cooling device(s) 108 and the generator 102. The feedback control may include the generator 102, the probes 107 and the cooling devices 108, although any feedback between any two devices is within the scope of the present invention. The feedback control may be implemented, for example, in a control module which may be a component of the generator 102. In such embodiments, the generator 102 is operable to communicate bi-directionally with the probes 107 as well as with the cooling devices 108. In the context of this invention, bi-directional communication refers to the capability of a device to both receive a signal from and send a signal to another device.

As an example, the generator 102 may receive temperature measurements from one or more of the plurality of probes 107. Based on the temperature measurements, the generator 102 may perform some action, such as modulating the power that is sent to the probes 107. Thus, the probes 107 may be individually controlled based on their respective temperature measurements. For example, power to each of the probes 107 can be increased when a temperature measurement is low or decreased when a measurement is high. This variation of power may be different for each probe assembly. In some cases, the generator 102 may terminate power to one or more probes 107. Thus, the generator 102 may receive a signal (e.g. temperature measurement) from one or more of probes 107, determine the appropriate action, and send a signal (e.g. decreased or increased power) back to one or more of the probes 107. Alternatively, the generator 102 may send a signal to the cooling devices 108 to either increase or decrease the flow rate or degree of cooling being supplied to one or more of the probes 107.

More specifically, the pumps may communicate a fluid flow rate to the generator 102 and may receive communications from the generator 102 instructing the pumps to modulate this flow rate. In some instances, the peristaltic pumps may respond to the generator 102 by changing the flow rate or turning off for a period of time. With the cooling devices 108 turned off, any temperature sensing elements associated with the probes 107 would not be affected by the cooling fluid allowing a more precise determination of the surrounding tissue temperature to be made. In addition, when using more than one probe assembly 106, the average temperature or a maximum temperature in the temperature sensing elements associated with probes 107 may be used to modulate cooling.

In other embodiments, the cooling devices 108 may reduce the rate of cooling or disengage depending on the distance between the probes 107. For example, when the distance is small enough such that a sufficient current density exists in the region to achieve a desired temperature, little or no cooling may be required. In such an embodiment, energy is preferentially concentrated between the energy delivery devices 192 through a region of tissue to be treated, thereby creating a strip lesion. A strip lesion is characterized by an oblong volume of heated tissue that is formed when an active electrode is near a return electrode of similar dimensions. This occurs because at a given power, the current density is preferentially concentrated between the electrodes and a rise in temperature results from current density.

The cooling devices 108 may also communicate with the generator 102 to alert the generator 102 to one or more possible errors and/or anomalies associated with the cooling devices 108. For example, if cooling flow is impeded or if a lid of one or more of the cooling devices 108 is opened. The generator 102 may then act on the error signal by at least one of alerting a user, aborting the procedure, and modifying an action.

Still referring to FIG. 1, the proximal cooling supply tubes 112 may include proximal supply tube connectors 116 at the distal ends of the one or more proximal cooling supply tubes 112. Additionally, the proximal cooling return tubes 114 may include proximal return tube connectors 118 at the distal ends of the one or more proximal cooling return tubes 114. In one embodiment, the proximal supply tube connectors 116 are female luer-lock type connectors and the proximal return tube connectors 118 are male luer-lock type connectors although other connector types are intended to be within the scope of the present invention.

In addition, as shown in FIG. 1, each of the probes 107 may include a proximal region 160, a handle 180, a hollow elongate shaft 184, and a distal tip region 190 that includes the one or more energy delivery devices 192. Further, as shown, the proximal region 160 includes a distal cooling supply tube 162, a distal supply tube connector 166, a distal cooling return tube 164, a distal return tube connector 168, a probe assembly cable 170, and a probe cable connector 172. In such embodiments, the distal cooling supply tube 162 and distal cooling return tube 164 are flexible to allow for greater maneuverability of the probes 107, but alternate embodiments with rigid tubes are possible.

Further, in several embodiments, the distal supply tube connector 166 may be a male luer-lock type connector and the distal return tube connector 168 may be a female luer-lock type connector. Thus, the proximal supply tube connector 116 may be operable to interlock with the distal supply tube connector 166 and the proximal return tube connector 118 may be operable to interlock with the distal return tube connector 168.

The probe cable connector 172 may be located at a proximal end of the probe assembly cable 170 and may be operable to reversibly couple to one of the connectors 140, thus establishing an electrical connection between the generator 102 and the probe assembly 106. The probe assembly cable 170 may include one or more conductors depending on the specific configuration of the probe assembly 106. For example, in one embodiment, the probe assembly cable 170 may include five conductors allowing probe assembly cable 170 to transmit RF current from the generator 102 to the one or more energy delivery devices 192 as well as to connect multiple temperature sensing devices to the generator 102 as discussed below.

The energy delivery devices 192 may include any means of delivering energy to a region of tissue adjacent to the distal tip region 190. For example, the energy delivery devices 192 may include an ultrasonic device, an electrode or any other energy delivery means and the invention is not limited in this regard. Similarly, energy delivered via the energy delivery devices 192 may take several forms including but not limited to thermal energy, ultrasonic energy, radiofrequency energy, microwave energy or any other form of energy. For example, in one embodiment, the energy delivery devices 192 may include an electrode. The active region of the electrode may be 2 to 20 millimeters (mm) in length and energy delivered by the electrode is electrical energy in the form of current in the RF range. The size of the active region of the electrode can be optimized for placement within an intervertebral disc, however, different sizes of active regions, all of which are within the scope of the present invention, may be used depending on the specific procedure being performed. In some embodiments, feedback from the generator 102 may automatically adjust the exposed area of the energy delivery device 192 in response to a given measurement such as impedance or temperature. For example, in one embodiment, the energy delivery devices 192 may maximize energy delivered to the tissue by implementing at least one additional feedback control, such as a rising impedance value.

Referring in detail to FIG. 2, a perspective cut-away view of one embodiment of the distal tip region 190 of the probe assembly 106 is illustrated. As shown, the distal tip region 190 includes one or more temperature sensing elements 402 which are operable to measure the temperature at and proximate to the one or more energy delivery devices 192. The temperature sensing elements 402 may include one or more thermocouples, thermometers, thermistors, optical fluorescent sensors or any other means of sensing temperature. In one embodiment, the temperature sensing elements 402 are connected to the generator 102 via probe assembly cable 170 and cable 104 although any means of communication between the temperature sensing elements 402 and the generator 102, including wireless protocols, are included within the scope of the present invention. More specifically, as shown, the temperature sensing element(s) 402 may include a thermocouple junction made by joining a stainless steel hypotube 406 to a constantan wire 410, wherein the constantan wire 410 is insulated by insulation 412. In this embodiment, the junction of hypotube 406 and the constantan wire 410 is made by laser welding, although any other means of joining two metals may be used. Furthermore, in this embodiment, the hypotube 406 and the constantan wire 410 extend through a lumen of the elongate shaft 184 and connect to the probe assembly cable 170 within the handle 180.

Further, as shown, the temperature sensing element 402 of each probe 107 protrudes beyond the energy delivery device 192. Placing the temperature sensing elements 402 at this location, rather than within a lumen 450 defined by the energy delivery device 192, is beneficial because it allows the temperature sensing element 402 to provide a more accurate indication of the temperature of tissue proximate to the energy delivery device 192. This is due to the fact that, when extended beyond the energy delivery device 192, the temperature sensing element 402 will not be as affected by the cooling fluid flowing within the lumen 450 as it would be were it located within lumen 450. Thus, in such embodiments, the probe assembly 106 includes a protrusion protruding from the distal region of the probe assembly, whereby the protrusion is a component of the temperature sensing element 402.

Referring still to FIG. 2, the probe assembly 106 may further include one or more secondary temperature sensing elements 404 located within the elongate shaft 184 at some distance away from the energy delivery device 192, and positioned adjacent a wall of the elongate shaft 184. The secondary temperature sensing elements 404 may similarly include one or more thermocouples, thermometers, thermistors, optical fluorescent sensors or any other means of sensing temperature. For example, as shown, the secondary temperature sensing element 404 is a thermocouple made by joining copper and constantan thermocouple wires, designated as 420 and 422 respectively. Further, in certain embodiments, the copper and constantan wires 420 and 422 may extend through a lumen of the elongate shaft 184 and may connect to the probe assembly cable 170 within the handle 180.

In addition, the probe assembly 106 may further include a thermal insulator 430 located proximate to any of the temperature sensing elements 402, 404. As such, the thermal insulator 430 may be made from any thermally insulating material, for example silicone, and may be used to insulate any temperature sensing element from other components of the probe assembly 106, so that the temperature sensing element will be able to more accurately measure the temperature of the surrounding tissue. More specifically, as shown, the thermal insulator 430 is used to insulate the temperature sensing element 404 from cooling fluid passing through the shaft supply tube 302 and the shaft return tube 304.

In further embodiments, the probe assembly 106 may also include a radiopaque marker 440 incorporated somewhere along the elongate shaft 184. For example, as shown in FIG. 2, an optimal location for a radiopaque marker may be at or proximate to the distal tip region 190, adjacent the energy delivery device 192. The radiopaque markers are visible on fluoroscopic x-ray images and can be used as visual aids when attempting to place devices accurately within a patient's body. These markers can be made of many different materials, as long as they possess sufficient radiopacity. Suitable materials include, but are not limited to silver, gold, platinum and other high-density metals as well as radiopaque polymeric compounds. Various methods for incorporating radiopaque markers into or onto medical devices may be used, and the present invention is not limited in this regard.

Further, as shown, the elongate shaft 184 and the electrode 192 overlap to secure the electrode in place. In this embodiment, the lumen defined by the elongate shaft 184 and the electrode 192 at this portion of the distal tip region 190 contains a radiopaque marker 440 made of silver solder, which fills the lumen such that any cooling fluid supplied to the probe assembly 106, that is not located within one of the cooling tubes described earlier, is confined to the distal tip region 190 of probe assembly 106. Thus, in such an embodiment, the silver solder may be referred to as a flow impeding structure since it functions to restrict the circulation of fluid to a specific portion (in this case, at least a portion of distal region 190) of the probe assembly 106.

In other words, cooling fluid may flow from the cooling devices 108, through the cooling supply tubes to the distal tip region 190 of the probe assembly 106. The cooling fluid may then circulate within the lumen 450 defined by the electrode 192 to provide cooling thereto. As such, the internally-cooled probe as described herein is defined as a probe having such a configuration, whereby a cooling medium does not exit probe assembly 106 from a distal region of probe assembly 106. The cooling fluid may not circulate further down the elongate shaft 184 due to the presence of the silver solder, and flows through the cooling return tubes back to the cooling devices 108. In alternate embodiments, other materials may be used instead of silver solder, and the invention is not limited in this regard. As described above, providing cooling to the probes 107 allows heat delivered through the energy delivery devices 192 to be translated further into the tissue without raising the temperature of the tissue immediately adjacent the energy delivery device 192.

As mentioned above, the system 100 of the present invention may further include one or more introducer tubes. Generally, introducer tubes may include a proximal end, a distal end, and a longitudinal bore extending therebetween. Thus, the introducer tubes (when used) are operable to easily and securely couple with the probe assembly 106. For example, the proximal end of the introducer tubes may be fitted with a connector able to mate reversibly with handle 180 of probe assembly 106. An introducer tube may be used to gain access to a treatment site within a patient's body and a hollow elongate shaft 184 of a probe assembly 106 may be introduced to said treatment site through the longitudinal bore of said introducer tube. Introducer tubes may further include one or more depth markers to enable a user to determine the depth of the distal end of the introducer tube within a patient's body. Additionally, introducer tubes may include one or more radiopaque markers to ensure the correct placement of the introducers when using fluoroscopic guidance.

The system may also include one or more stylets. A stylet may have a beveled tip to facilitate insertion of the one or more introducer tubes into a patient's body. Various forms of stylets are well known in the art and the present invention is not limited to include only one specific form. Further, as described above with respect to the introducer tubes, the stylets may be operable to connect to a power source and may therefore form part of an electrical current impedance monitor. In other embodiments, one or more of the probe assemblies 106 may form part of an electrical current impedance monitor. Thus, the generator 102 may receive impedance measurements from one or more of the stylets, the introducer tubes, and/or the probes 107 and may perform an action, such as alerting a user to an incorrect placement of an energy delivery device 192, based on the impedance measurements.

In addition, as shown in FIGS. 4-6, the generator 102 may also include a user interface 142 that displays various aspects of a treatment procedure, including but not limited to any parameters that are relevant to a treatment procedure, such as temperature, impedance, etc. and errors or warnings related to a treatment procedure. More specifically, as shown, the user interface 142 includes a collapsible control screen 144. Further, as shown, the control screen 144 includes an independent control module 146 and a simultaneous control module 148 that allows a user to select between independent control or simultaneous control of the plurality of probes 107. Thus, the system described herein improves procedure efficiency by enabling the user to start all connected probes 107 simultaneously (i.e. through the use of a single control) or each individually.

Referring particularly to FIG. 4, the simultaneous control module 148 may include a simultaneous control selection panel 150 that, upon selection by the user, is configured to start a treatment procedure for each of the plurality of probes 107 simultaneously. In certain embodiments, as shown, the simultaneous control selection panel 150 may include a simultaneous control sliding bar 152. Similarly, as shown, the independent control module 146 may include an independent control selection panel 154 that, upon selection by the user, is configured to collapse the control screen 144 and switch to an independent control screen 156. The user can easily move between screens by simply clicking on a collapsed screen to reengage the collapsed screen once again, e.g. via control arrow 155. As such, the simultaneous or independent start is enabled by engaging the control arrow 155 on the collapsible control screen 144 and the sliding menu panel 152. More specifically, as shown, the panel 152 displays a single control to start all connected probes 107 simultaneously and can be collapsed through a control (e.g. sliding motion by the user or through the selection of a labeled button instructing the user to select whether to start each probe 107 individually).

As shown in FIG. 5, the user can control the probes 107 individually via the independent control screen 156. More specifically, as shown particularly in FIG. 5, the independent control screen 156 may include an independent control panel 158 for each of the plurality of probes 107. In such embodiments, each of the independent control panels 158 may include an independent sliding bar 163 that, upon engagement or selection by the user, is configured to start a treatment procedure for the selected probe 107 from the plurality of probes 107.

For example, in certain embodiments, in order to start a probe 107 independently, the user can collapse the control screen 144 and individual start buttons 163 are configured to appear for each channel. Thus, in one embodiment, the user interface 142 enables individual start of the probes 107 by incorporating a "swim lane" concept for each channel. As used herein, the "swim lane" concept generally refers to the idea of having controls for each probe 107 displayed in a separate lane or panel and allowing the treatment procedure for each probe 107 to run or operate in its respective lane such that it can be compared to other operating probes 107 as well. Thus, as shown particularly in FIG. 5, each lane horizontally depicts the characteristics and required data points for that lane. Further, as shown in the illustrated embodiment, the individual start buttons 163 for each lane may be located at the end of each lane.

In further embodiments, as shown in FIGS. 4-6, the simultaneous control selection panel 150 and/or each of the independent control panels 158 may include a display 165 for displaying one or more real-time operating parameters 171 of the treatment procedure. For example, as shown, the real-time operating parameters 171 may include an actual temperature, an impedance, an actual time, a run time, a power output of the associated energy delivery device 192, a threshold temperature, or combinations thereof. In several embodiments, each of the independent control panels 158 may also include one or more buttons 167 for allowing the user to modify one or more of the operating parameters. In addition, the swim lane concept also enables stopping of individual probes 107. For example, as shown, each lane may contain a stop button 169 for the related probe 107, or all probes 107 can be stopped simultaneous through a single control on the system, so as to stop the treatment procedure of the associated probe.

In one embodiment, the plurality of probes 107 may be operated in a bipolar mode. For example, FIG. 7 illustrates one embodiment of two probes 107, wherein the distal tip regions 190 thereof are located within an intervertebral disc 800. In such embodiments, electrical energy is delivered to the probes 107 and this energy is preferentially concentrated therebetween through a region of tissue to be treated (i.e. an area of the intervertebral disc 800). The region of tissue to be treated is thus heated by the energy concentrated between the probes 107. In other embodiments, the probes 107 may be operated in a monopolar mode, in which case an additional grounding pad is required on the surface of a body of a patient, as is known in the art. Any combination of bipolar and monopolar procedures may also be used. It should also be understood that the system may include more than two probe assemblies. For example, in some embodiments, three probe assemblies may be used and the probe assemblies may be operated in a triphasic mode, whereby the phase of the current being supplied differs for each probe assembly.

Referring now to FIG. 8, a flow diagram of one embodiment of a method 500 for treating tissue of a patient's body, such as an intervertebral disc 800, using the probe assemblies described herein is illustrated. As shown at 502, the method 500 may include providing an energy source coupled to a probe assembly 106 having a plurality of probes 107, such as those described herein. As shown at 504, the method 500 further includes communicatively coupling a controller (e.g. such as the generator 102) to the probe assembly 106. Further, as mentioned, the generator 102 includes the user interface 142 that displays the collapsible control screen 144. As shown 506, the method 500 includes inserting the plurality of probes 107 into the patient's body. As shown at 508, the method 500 includes positioning the plurality of probes 107 at the tissue of the patient's body to be treated. For example, in one embodiment, with a patient lying on a radiolucent table, fluoroscopic guidance may be used to percutaneously insert an introducer with a stylet to access the posterior of an intervertebral disc. In addition to fluoroscopy, other aids, including but not limited to impedance monitoring and tactile feedback, may be used to assist a user to position the introducer or probes 107 within the patient's body. The use of impedance monitoring has been described herein, whereby a user may distinguish between tissues by monitoring impedance as a device is inserted into the patient's body. With respect to tactile feedback, different tissues may offer different amounts of physical resistance to an insertional force. This allows a user to distinguish between different tissues by feeling the force required to insert a device through a given tissue.

As shown at 510, the method 500 includes selecting whether to operate the plurality of probes 107 independently or simultaneously via the independent control module 146 and the simultaneous control module 148. As shown at 512, the method 500 includes treating the tissue by controlling the plurality of probes 107 based on the selection. Once in place, a stimulating electrical signal may be emitted from the probes 107 to stimulate sensory nerves where replication of symptomatic pain would verify that the disc is pain-causing.

During the procedure, a treatment protocol such as the cooling supplied to the probes 107 and/or the power transmitted to the probes 107 may be adjusted and/or controlled to maintain a desirable treatment area shape, size and uniformity. More specifically, the method 500 includes actively controlling energy delivered to the tissue by controlling both an amount of energy delivered through the energy delivery devices 192 and individually controlling the flow rate of the peristaltic pumps 122. In further embodiments, the generator 102 may control the energy delivered to the tissue based on the measured temperature measured by the temperature sensing element(s) 402 and/or impedance sensors.

More specifically, as shown in FIG. 9, a block diagram of one embodiment of a treatment procedure for treating a patient's tissues is illustrated. As shown at 600, ablation is initialized. As shown at 602, the energy dosage may be calculated using simple numerical integration techniques. As shown at 604, the calculated energy dosage may then be compared against a preset energy dosage threshold. If the dosage is not satisfied as shown at 606, the procedure continues to 608 to mitigate rising impedance of the internally-cooled probes 107 during the treatment procedure. More specifically, as shown, one or more procedure parameters are monitored while delivering the energy from the generator 102 to the tissue through the energy delivery devices 192. The procedure parameter(s) described herein may include, for example, a temperature of the tissue, an impedance of the tissue, a power demand of the energy delivery device 192, or similar, or combinations thereof. Further, as shown, the procedure parameter(s) 608 may be fed into a rising impedance detection engine 610. As shown at 612, the rising impedance detection engine 610 is configured to determine, e.g. in real-time, whether a rising impedance event is likely to occur in a predetermined time period (i.e. whether the rising impedance event is imminent) based on the received procedure parameter(s) 608. The rising impedance detection engine 610 can then determine a command for the pump assembly 120 based on whether the rising impedance event is likely to occur in the predetermined time period.

If not imminent, as shown at 614, the cooling rate can be increased, e.g. by increasing the pump speed (e.g. via the RPM controllers 125) of the peristaltic pumps 122 as shown at 616. After the cooling rate is increased, the ablation 600 continues. If a rising impedance event is imminent, as shown at 618, the cooling rate can be reduced, e.g. by decreasing the pump speed (e.g. via the RPM controllers 125) of the peristaltic pumps 122 as shown at 620. In other words, in several embodiments, the peristaltic pumps 122 may be independently controlled via their respective RPM controllers 125 to alter the rate of cooling to each electrode 192 of the probes 107. In such embodiments, the power supply 126 of the pump assembly 120 may be decoupled, at least in part, from the generator 102. Further, as shown, the system 550 operates using closed-loop feedback control 634, 636.

Once the energy dosage threshold is satisfied, as shown at 622, the treatment procedure is configured to check if the thermal dosage threshold has been satisfied as shown at 624. If the thermal dosage has not been satisfied, as shown at 626, the treatment procedure proceeds through the independent temperature-power feedback control loop as shown at 628. More specifically, in certain embodiments, the amount of energy delivered through the energy delivery device 192 may be controlled by defining a predetermined threshold temperature for treating the tissue, ramping up the temperature of the tissue via the generator 102 through the energy delivery device 192 to the predetermined threshold temperature, and maintaining the temperature of the tissue at the predetermined threshold temperature to create a lesion in the tissue. In such embodiments, the temperature of the tissue may be maintained at the predetermined threshold temperature as a function of at least one of a power ramp rate, an impedance level, an impedance ramp rate, and/or a ratio of impedance to power.

Only when the thermal dosage threshold has been satisfied, as shown at 630, the procedure terminates as shown at 632. Thus, the system and method of the present disclosure provides the unique features of probe(s) with inherently high-power demand (i.e. short thermocouple protrusion), a pump-modulated power algorithm, a preset energy dosage or total average power threshold, and/or a rising impedance detection engine 610.

Following treatment, energy delivery and cooling may be stopped and the probes 107 are removed from the introducers, where used. A fluid such as an antibiotic or contrast agent may be injected through the introducers, followed by removal of the introducers. Alternatively, the distal tips of the probes 107 may be sharp and sufficiently strong to pierce tissue so that introducers may not be required. As mentioned above, positioning the probes 107, and more specifically the energy delivery devices 192, within the patient's body, may be assisted by various means, including but not limited to fluoroscopic imaging, impedance monitoring and tactile feedback. Additionally, some embodiments of this method may include one or more steps of inserting or removing material into a patient's body.

A system of the present invention may be used in various medical procedures where usage of an energy delivery device may prove beneficial. Specifically, the system of the present invention is particularly useful for procedures involving treatment of back pain, including but not limited to treatments of tumors, intervertebral discs, facet joint denervation, sacroiliac joint lesioning or intraosseous (within the bone) treatment procedures. Moreover, the system is particularly useful to strengthen the annulus fibrosus, shrink annular fissures and impede them from progressing, cauterize granulation tissue in annular fissures, and denature pain-causing enzymes in nucleus pulposus tissue that has migrated to annular fissures. Additionally, the system may be operated to treat a herniated or internally disrupted disc with a minimally invasive technique that delivers sufficient energy to the annulus fibrosus to breakdown or cause a change in function of selective nerve structures in the intervertebral disc, modify collagen fibrils with predictable accuracy, treat endplates of a disc, and accurately reduce the volume of intervertebral disc tissue. The system is also useful to coagulate blood vessels and increase the production of heat shock proteins.

Using liquid-cooled probes 107 with an appropriate feedback control system as described herein also contributes to the uniformity of the treatment. The cooling distal tip regions 190 of the probes 107 helps to prevent excessively high temperatures in these regions which may lead to tissue adhering to the probes 107 as well as an increase in the impedance of tissue surrounding the distal tip regions 190 of the probes 107. Thus, by cooling the distal tip regions 190 of the probes 107, higher power can be delivered to tissue with a minimal risk of tissue charring at or immediately surrounding the distal tip regions 190. Delivering higher power to energy delivery devices 192 allows tissue further away from the energy delivery devices 192 to reach a temperature high enough to create a lesion and thus the lesion will not be limited to a region of tissue immediately surrounding the energy delivery devices 192 but will rather extend preferentially from a distal tip region 190 of one probe assembly 106 to the other.

It should be noted that the term radiopaque marker as used herein denotes any addition or reduction of material that increases or reduces the radiopacity of the device. Furthermore, the terms probe assembly, introducer, stylet etc. are not intended to be limiting and denote any medical and surgical tools that can be used to perform similar functions to those described. In addition, the invention is not limited to be used in the clinical applications disclosed herein, and other medical and surgical procedures wherein a device of the present invention would be useful are included within the scope of the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A system for delivering energy to a patient's body, the system comprising:

a plurality of probes each comprising an elongate member having a distal region with an electrically non-conductive outer circumferential portion and a proximal region, each of the plurality of probes further comprising an electrically conductive energy delivery device extending distally from said electrically non-conductive outer circumferential portion for delivering one of electrical and radiofrequency energy to the patient's body and having an electrically conductive outer circumferential surface; and at least one controller communicatively coupled to each of the plurality of probes, the controller comprising a user interface comprising a display showing treatment parameters and a collapsible control screen, the collapsible control screen comprising a simultaneous control selection panel and an independent control selection panel, wherein the simultaneous control selection panel starts a treatment procedure for all of the plurality of probes simultaneously, and wherein the independent control selection panel collapses the collapsible control screen and switches to an independent control screen comprising independent control panels corresponding to each of the plurality of probes that, upon selection by the user, each start an individual treatment procedure for a selected independent control panel of one of the plurality of probes, wherein the user interface includes the display showing one or more real-time operating parameters with the collapsible control screen and/or the independent control screen.

2. The system of claim 1, wherein the simultaneous control selection panel comprises a simultaneous control sliding bar.

3. The system of claim 1, wherein the collapsible control screen further comprises a control arrow that, when swiped in a first direction by a user, collapses the collapsible control screen.

4. The system of claim 3, wherein, if the user wants to reopen the collapsed collapsible control screen, the user can swipe the control arrow in a second direction.

5. The system of claim 1, wherein the independent control panel for each of the plurality of probes comprises an independent sliding bar that, upon selection by the user, is configured to start a treatment procedure for one of the probes from the plurality of probes.

6. The system of claim 1, wherein the one or more real-time operating parameters comprises at least one of an actual temperature, an impedance, an actual time, a run time, a power output of the energy delivery device, a threshold temperature, or combinations thereof.

7. The system of claim 1, wherein the simultaneous control selection panel and/or each of the independent control panels further comprises one or more buttons for allowing the user to modify one or more of the operating parameters.

8. The system of claim 7, wherein one of the one or more buttons further comprises a stop button for stopping the treatment procedure.

9. The system of claim 1, wherein the display showing one or more real-time operating parameters is beside the collapsible control screen and/or the independent control screen on the user interface.

10. A method of treating tissue of a patient's body, the method comprising:

providing an energy source coupled to a probe assembly, the probe assembly comprising a plurality of probes, each probe having an elongate member with a distal region and a proximal region, the distal region having an electrically-conductive energy delivery device for delivering one of electrical and radiofrequency energy to the patient's body;

communicatively coupling a controller to the probe assembly, the controller having a user interface with a collapsible control screen and a display, the collapsible control screen having an independent control selection panel and a simultaneous control selection panel;

inserting the plurality of probes into the patient's body;
positioning the plurality of probes at the tissue of the patient's body;

selecting whether to operate the plurality of probes independently or simultaneously via the independent control selection panel and the simultaneous control selection panel;

showing one or more real-time operating parameters on the display within the user interface of the controller;

providing the collapsible control screen on the user interface along with the display;

collapsing the collapsible control screen upon selection of the independent control selection panel; and after collapsing the collapsible control screen, displaying an independent control screen and the treatment parameters on the display within the user interface.

11. The method of claim 10, wherein the simultaneous control selection panel comprises a simultaneous control sliding bar.

12. The method of claim 10, wherein the independent control screen comprises an independent control panel for each of the plurality of probes, the independent control panel for each of the plurality of probes comprising an independent sliding bar that, upon selection by the user, is configured to start a treatment procedure for one of the probes from the plurality of probes.

13. The method of claim 12, wherein each of the independent control panels further comprises one or more buttons, the method further comprising pressing the one or more buttons to modify one or more of the operating parameters.

14. The method of claim 10, wherein the one or more real-time operating parameters comprise at least one of an actual temperature, an impedance, an actual time, a run time, a power output of the energy delivery device, a threshold temperature, or combinations thereof.

15. The method of claim 10, wherein the collapsible control screen further comprises a control arrow that, when swiped in a first direction by a user, collapses the collapsible control screen, wherein, if the user wants to reopen the collapsed collapsible control screen, the user can swipe the control arrow in a second direction.

16. The method of claim 10, wherein the display showing one or more real-time operating parameters is simultaneously shown beside the collapsible control screen and/or the independent control screen.

17. A controller for controlling a plurality of radiofrequency probes during a treatment procedure, the controller comprising:

a user interface comprising a display showing one or more real-time operating parameters and a collapsible control screen, the control screen comprising an independent control selection panel and a simultaneous control selection panel, wherein the simultaneous control selection panel starts a treatment procedure for each of the plurality of probes simultaneously, wherein the independent control selection panel collapses the collapsible control screen and switches to an independent control screen comprising an independent control panel for each of the plurality of probes that, upon selection by the user, starts an individual treatment procedure for a selected independent control panel of one of the plurality of probes, and wherein the user interface includes the display showing the one or more real-time operating parameters with the collapsible control screen and/or the independent control screen.

18. The controller of claim 17, wherein the display showing one or more real-time operating parameters is beside the collapsible control screen and/or the independent control screen on the user interface.

19. The controller of claim 17, wherein the one or more real-time operating parameters comprises at least one of an actual temperature, an impedance, an actual time, a run time, a power output of the energy delivery device, a threshold temperature, or combinations thereof.

20. The controller of claim 17, wherein the independent control screen comprises an independent control panel for each of the plurality of radiofrequency probes, the independent control panel for each of the plurality of probes comprising an independent sliding bar that, upon selection by the user, is configured to start a treatment procedure for one of the radiofrequency probes from the plurality of radiofrequency probes.

* * * * *